United States Patent [19]
Dornhagen et al.

[11] Patent Number: 5,789,557
[45] Date of Patent: Aug. 4, 1998

[54] REACTIVE AZO DYES WITH A COUPLER OF THE AMINONAPHTHALENE SERIES

[75] Inventors: Jürgen Dornhagen, Limburgerhof; Heike Kilburg, Speyer; Manfred Patsch, Wachenheim; Hermann Löffler, Speyer; Ortwin Schaffer, Ludwigshafen, all of Germany

[73] Assignee: Basf Aktiengesellschaft, Ludwigshafen, Germany

[21] Appl. No.: 809,292

[22] PCT Filed: Sep. 19, 1995

[86] PCT No.: PCT/EP95/03687

§ 371 Date: Mar. 27, 1997

§ 102(e) Date: Mar. 27, 1997

[87] PCT Pub. No.: WO96/10610

PCT Pub. Date: Apr. 11, 1996

[30] Foreign Application Priority Data

Sep. 30, 1994 [DE] Germany ............... 44 34 989.0

[51] Int. Cl.⁶ .................. C09B 62/507; C09B 62/08; D06P 1/38; C07C 309/47
[52] U.S. Cl. .................. 534/634; 534/638; 534/641; 534/642; 562/43; 562/55
[58] Field of Search .................. 534/634, 638, 534/641, 642; 562/43, 55

[56] References Cited

U.S. PATENT DOCUMENTS

| | | | |
|---|---|---|---|
| 1,864,425 | 6/1932 | Fritzsche | 562/43 |
| 3,925,351 | 12/1975 | Meininger et al. | 534/642 |
| 4,002,606 | 1/1977 | Schlafer et al. | 534/642 |
| 4,036,825 | 7/1977 | Fuchs et al. | 534/642 |
| 4,066,638 | 1/1978 | Fuchs et al. | 534/642 |
| 4,134,887 | 1/1979 | Fuchs et al. | 534/642 |
| 4,248,776 | 2/1981 | Papa et al. | 534/810 |
| 5,023,326 | 6/1991 | Tzikas et al. | 534/638 |
| 5,439,517 | 8/1995 | Yoshida et al. | 106/31.48 |
| 5,569,748 | 10/1996 | Reiher et al. | 534/642 |
| 5,647,897 | 7/1997 | Ouki et al. | 106/31.49 |
| 5,681,937 | 10/1997 | Patsch et al. | 534/642 |

FOREIGN PATENT DOCUMENTS

| | | |
|---|---|---|
| 369385 | 5/1990 | European Pat. Off. |
| 2221496 | 10/1974 | France |
| 2242377 | 3/1975 | France |
| 2248301 | 5/1975 | France |
| 2424304 | 11/1979 | France |
| 2429243 | 1/1980 | France |
| 1220060 | 6/1966 | Germany |
| 567084 | 9/1975 | Switzerland |
| 2053261 | 2/1981 | United Kingdom |

OTHER PUBLICATIONS

Kosower et al., J. Am. Chem. Soc., 96:19, Sep. 18, 1974, 6195–6196.
Colour Index, Third Edition, vol. 4, p. 4801, 1971.
Morris et al., Chemical Abstracts, 60:12029d (1964).
McKay et al., Chemical Abstracts, 61:8445h (1964).
Ames et al., Chemical Abstracts, 53:5608 f (1959).

*Primary Examiner*—Fiona T. Powers
*Attorney, Agent, or Firm*—Oblon, Spivak, McClelland, Maier & Neustadt, P.C.

[57] ABSTRACT

Reactive dyes of the formula

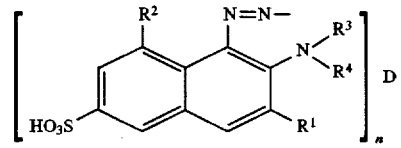

where
n is 1 or 2,
$R^1$ is hydrogen or hydroxysulfonyl,
$R^2$ is hydrogen or hydroxyl,
$R^3$ is substituted $C_1$–$C_4$-alkyl, $C_5$–$C_7$-cycloalkyl or substituted phenyl,
$R^4$ is hydrogen or $R^3$ and $R^4$, together with the nitrogen atom linking them, form a heterocyclic radical and
D is a radical of a diazo or tetrazo component, each having at least one mechanism,
their use for dyeing or printing hydroxyl-containing or nitrogen-containing organic substrates, and novel aminonaphthalenes.

10 Claims, No Drawings

REACTIVE AZO DYES WITH A COUPLER OF THE AMINONAPHTHALENE SERIES

This application is a 371 of PCT/EP95/03687 filed Sep. 19, 1995.

The present invention relates to novel reactive dyes of the formula I

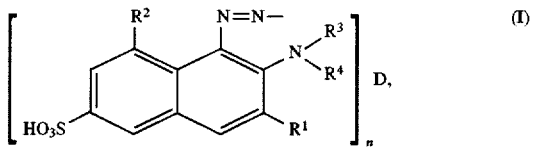

where
n is 1 or 2,
$R^1$ is hydrogen or hydroxysulfonyl,
$R^2$ is hydrogen or hydroxyl,
$R^3$ is carboxymethyl, hydroxysulfonylmethyl, a radical of the formula $W^1$—$SO_2$—Y or $W^2$(—$SO_2$—Y)$_2$, where $W^1$ is $C_1$-$C_4$-alkylene or unsubstituted or substituted phenylene, $W^2$ is a trivalent radical of a benzene ring which is unsubstituted or substituted and Y is vinyl or a radical of the formula $C_2H_4$—Q, where Q is a group which can be eliminated under alkaline reaction conditions, $C_5$-$C_7$-cycloalkyl or phenyl which is substituted by $C_1$-$C_4$-alkyl, $C_1$-$C_4$-alkoxy, carboxyl or a radical of the formula CONH—$W^1$—$SO_2$—Y or $SO_2$—Y, where $W^1$ and Y each have the abovementioned meanings, or, if n is 2, $R^3$ may furthermore be carboxy—$C_2$-$C_4$-alkyl or hydroxysulfonyl—$C_2$-$C_4$-alkyl,
$R^4$ is hydrogen or $R^3$ and $R^4$, together with the nitrogen atom linking them, form a 5-membered or 6-membered saturated heterocyclic radical which may have further hetero atoms, and
D, if n is 1, is a radical of the formula

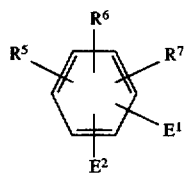

or, if n is 2, is a radical of the formula

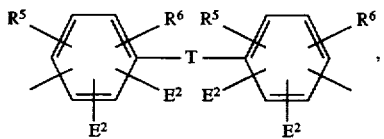

where $R^5$, $R^6$ and $R^7$, independently of one another, are each hydrogen, $C_1$-$C_4$-alkyl, $C_1$-$C_4$-alkoxy or hydroxysulfonyl, $E^1$ is a heterocyclic mechanism or a mechanism from the aliphatic series, $E^2$ is hydrogen or $E^1$, and T is a bridge member,
with the proviso that at least one mechanism is present in D, their use for dyeing or printing hydroxyl-containing or nitrogen-containing organic substrates, and novel aminonaphthalenes.

EP-A-369 385 discloses azo-based reactive dyes which contain 1-hydroxy-3-hydroxysulfonyl-7-(2-cyano-, 2-hydroxysulfonyl- or 2-carbamoylethylamino)naphthalene as a coupling component.

Furthermore, DE-A-2 154 942 and DE-A-2 163 389 describe reactive dyes of this class having 1-hydroxy-3-hydroxysulfonyl-7-methyl- or phenylaminonaphthalene as a coupling component.

It is an object of the present invention to provide novel reactive dyes which are derived from phenylazonaphthalene dyes. The novel dyes should have advantageous performance characteristics.

We have found that this object is achieved by the reactive dyes of the formula I which are defined at the outset.

The novel reactive dyes of the formula I are each present in the form of the free acid. Of course, the claims also relate to the salts thereof.

Suitable cations are derived from metal or ammonium ions. Metal ions are in particular the lithium, sodium or potassium ions. For he purposes of the present invention, ammonium ions are to be understood as meaning unsubstituted or substituted ammonium cations. Substituted ammonium cations are, for example, monoalkyl-, dialkyl-, trialkyl-, tetraalkyl- or benzyltrialkyl- ammonium cations or cations which are derived from nitrogen-containing 5- or 6-membered saturated heterocycles, such as pyrrolidinium, piperidinium, morpholinium, piperazinium or N-alkylpiperazinium cations or the N-monoalkyl- or N,N-dialkyl-substituted products thereof. Alkyl is to be understood in general as meaning straight-chain or branched $C_1$-$C_{20}$-alkyl which may be substituted by hydroxyl and/or interrupted by from 1 to 4 oxygen atoms as an ether function.

All alkyl and alkylene radicals occurring in the abovementioned formula I may be either straight-chain or branched.

If substituted alkyl groups occur in the abovementioned formula I, they have, as a rule, 1 or 2 substituents.

If substituted phenyl, phenylene or benzenetriyl groups occur in the abovementioned formula, suitable substituents are, for example, $C_1$-$C_4$-alkyl, $C_1$-$C_4$-alkoxy, halogen, hydroxysulfonyl, sulfamoyl or $C_1$-$C_4$-mono- or dialkylsulfamoyl, unless stated otherwise. In this case, they have, as a rule, from 1 to 3, preferably 1 or 2, substituents.

If $R^3$ and $R^4$, together with the nitrogen atom linking them, form a 5-membered or 6-membered saturated heterocyclic radical which may have further hetero atoms, suitable radicals of this type are, for example, pyrrolidinyl, piperidinyl, morpholinyl, thiomorpholinyl, thiomorpholinyl S,S-dioxide, piperazinyl or N-($C_1$-$C_4$-alkyl) piperazinyl, such as N-methyl- or N-ethylpiperazinyl.

$R^5$, $R^6$ and $R^7$ are each, for example, methyl, ethyl, propyl, isopropyl, butyl, isobutyl, sec-butyl, tert-butyl, methoxy, ethoxy, propoxy, isopropoxy, butoxy, isobutoxy or sec-butoxy.

$W^1$ is, for example, $CH_2$, $(CH_2)_2$, $(CH_2)_3$, $(CH_2)_4$, $CH(CH_3)CH_2$, $CH(CH_3)CH(CH_3)$ or 1,2-, 1,3- or 1,4-phenylene.

$W^2$ is, for example, benzene-1,2,3-, -1,3,4- or -1,3,5-triyl.

$R^3$ is, for example, hydroxysulfonylmethyl, 2-hydroxysulfonylethyl, carboxymethyl, 1- or 2-carboxyethyl, a radical of the formula $C_2H_4$—$SO_2$—Y or $C_3H_6$—$SO_2$—Y, cyclopentyl, cyclohexyl, cycloheptyl, 2-, 3- or 4-methylphenyl, 2-, 3- or 4-ethylphenyl, 2-, 3- or 4-pro- pylphenyl, 2-, 3- or 4-isopropylphenyl, 2-, .3- or 4-butylphenyl, 2,3-, 2,4- or 2,6-dimethylphenyl, 2-methyl-6-ethylphenyl, 2-, 3- or 4carboxyphenyl or a radical of the formula

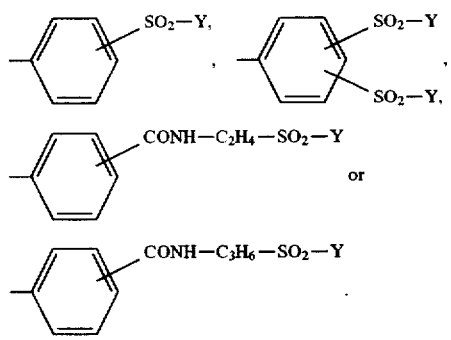

Q is a group which can be eliminated under alkaline reaction conditions. Such groups are, for example, chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, unsubstituted or substituted phenylsulfonyloxy, $C_1$–$C_4$-alkanoyloxy, $C_1$–$C_4$-dialkylamino or a radical of the formula

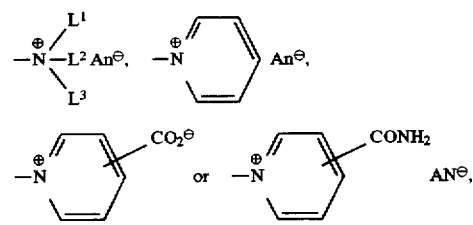

where $L^1$, $L^2$ and $L^3$, independently of one another, are each $C_1$–$C_4$-alkyl or benzyl and $An^\ominus$ in each case is one equivalent of an anion. Suitable anions are, for example, fluoride, chloride, bromide, iodide, mono-, di- and trichloroacetate, methanesulfonate, benzenesulfonate and 2- or 4-methylbenzenesulfonate. Mechanisms $E^1$ and $E^2$ are those which undergo a substitution or addition reaction with the hydroxyl-containing or nitrogen-containing groups of the substrates to be treated.

That the mechanism undergoes a substitution reaction with the relevant groups in the substrates, for example with the hydroxyl groups of cellulose, means that the leaving groups or leaving atoms (for example fluorine and chlorine) in the mechanism are substituted by the hydroxyl groups of the cellulose according to the following scheme:

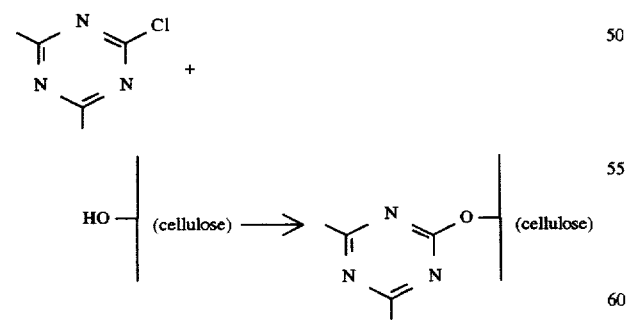

That the mechanism undergoes an addition reaction with the relevant groups in the substrates, for example with hydroxyl groups of cellulose, means that the hydroxyl groups of the cellulose undergo addition at the mechanism according to the following scheme:

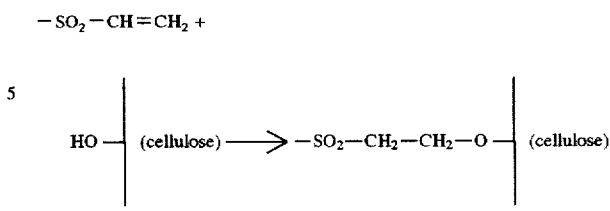

Heterocyclic mechanisms $E^1$ and $E^2$ are, for example, halogen-substituted radicals of 1,3,5-triazine, quinoxaline, phthalazine, pyrimidine or pyridazone, or a 2-alkylsulfonylbenzothiazole radical.

Examples are the following heterocyclic radicals:

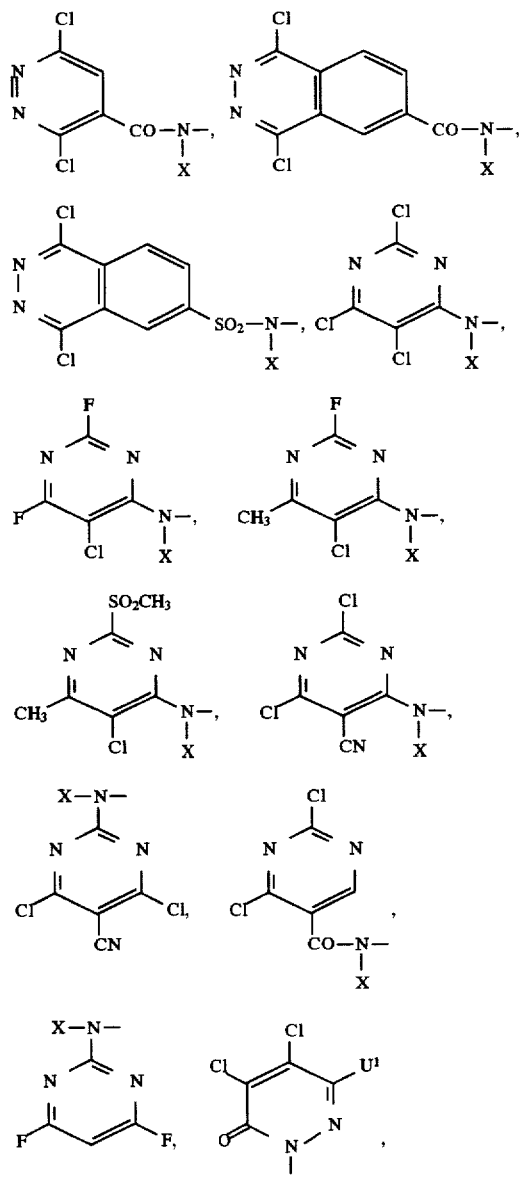

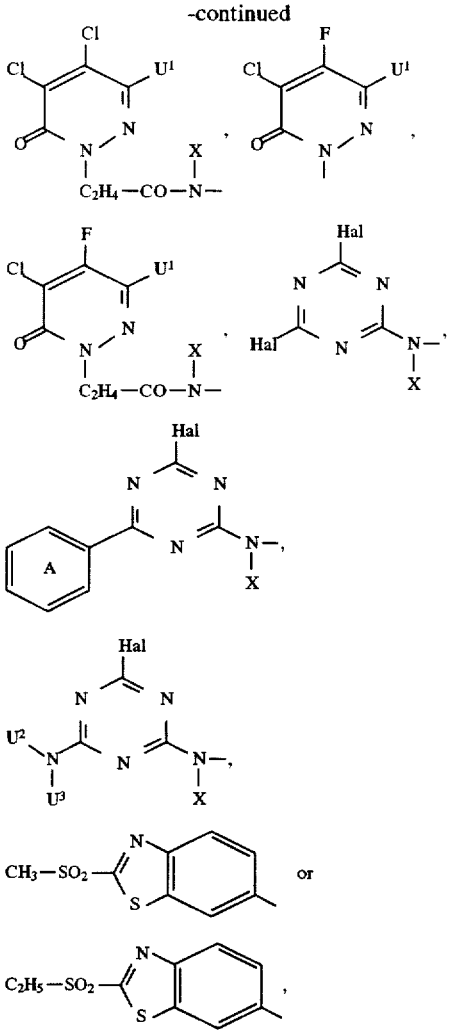

where

X is hydrogen or $C_1$–$C_4$-alkyl,

Hal is fluorine or chlorine, $U^1$ is hydrogen or nitro and $U^2$ and $U^3$, independently of one another, are each hydrogen or $C_1$–$C_6$-alkyl which is unsubstituted or substituted by hydroxyl, halogen, cyano, hydroxysulfonyl or a radical of the formula —$SO_2$—Y, where Y has the abovementioned meanings, and which may be interrupted by 1 or 2 oxygen atoms as an ether function, by imino or by $C_1$–$C_4$-alkylimino, or $U^2$ and $U^3$, together with the nitrogen atom linking them, form pyrrolidinyl, piperidinyl, morpholinyl, piperazinyl or N-($C_1$–$C_4$-alkyl)piperazinyl or $U^2$ may furthermore be a radical of the formula

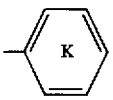

where the rings A and K may each be monosubstituted or disubstituted by hydroxysulfonyl and may each be benzofused and, independently thereof, the ring K may be monosubstituted or disubstituted by chlorine, nitro, $C_1$–$C_4$-alkyl, $C_1$–$C_4$-alkoxy, cyano, carboxyl, acetylamino, hydroxysulfonyl- methyl or a radical of the formula $CH_2$—$SO_2$—Y, $SO_2$—Y, NH—CO—Y or $NU^2$—CO—$NU^2$—Z—$SO_2$—Y, where Y and $U^2$ each have the abovementioned meanings, and Z is $C_2$–$C_6$-alkylene which is unsubstituted or substituted by hydroxyl, chlorine, cyano, carboxyl, $C_1$–$C_4$-alkoxycarbonyl, $C_1$–$C_4$-alkanoyloxy or sulfato and may be interrupted by 1 or 2 oxygen atoms as an ether function or by imino or $C_1$–$C_4$-alkylimino.

Mechanisms $E^1$ and $E^2$ from the aliphatic series are, for example, acryloyl, mono-, di- or trichloroacryloyl, mono-, di- or tri- bromoacryloyl, —CO—CCl=CH—COOH, —CO—CH=CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-fluoro-2-chloro-3,3-difluorocyclobut-1-ylcarbonyl, 2,2,3,3-tetrafluorocyclobut-1-ylcarbonyl, 2,2,3,3-tetrafluorocyclobut-1-ylsulfonyl, 2-(2,2,3,3-tetrafluoro- cyclobut-1-yl)acryloyl, 1- or 2-alkylsulfonylacryloyl or 1- or 2-arylsulfonylacryloyl, such as 1- or 2-methylsulfonylacryloyl, or a radical of the formula $SO_2$—Y, CONH—$W^1$—$SO_2$—Y or NHCONH—$W^1$—$SO_2$—Y, where $W^1$ and Y each have the abovementioned meanings.

In the formula I, T is a bridge member. Suitable bridge members are, for example, of the formula

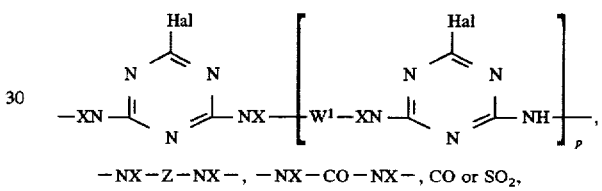

—NX—Z—NX—, —NX—CO—NX—, CO or $SO_2$, where p is 0 or 1 and Hal, $W^1$, X and Z each have the abovementioned meanings.

Particular examples of bridge members are radicals of the formula

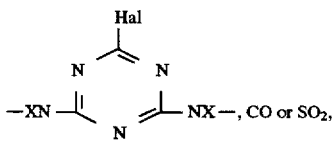

CO and $SO_2$ being noteworthy.

If n is 2, D is preferably of the formula

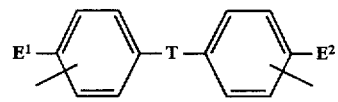

where $E^1$, $E^2$ and T each have the abovementioned meanings.

Preferred reactive dyes are those of the formula I where $R^1$ is hydrogen.

Reactive dyes of the formula I where $R^2$ is hydroxyl are also preferred.

Other preferred reactive dyes are those of the formula I where $R^3$ is hydroxysulfonylmethyl.

Reactive dyes of the formula I where $R^5$, $R^6$ and $R^7$ are each hydrogen are furthermore preferred.

Further preferred reactive dyes are those of the formula I where $E^1$ is a halogen-substituted radical of 1,3,5-triazine or a radical of the formula $SO_2$—Y, where Y has the abovementioned meanings.

Reactive dyes of the formula I where T is a radical of the formula CO or SO$_2$ if n is 2 are also preferred.

Reactive dyes of the formula I where n is 1 are furthermore preferred.

Other preferred reactive dyes are those of the formula I where E$^1$ is a radical of the formula

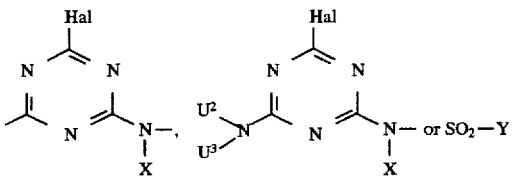

where Hal, U$^2$, U$^3$, X and Y each have the abovementioned meanings.

Particularly preferred reactive dyes are those of the formula I where E$^1$ is a radical of the formula SO$_2$—Y, where Y has the abovementioned meanings, and is ortho to the azo group.

Other particularly preferred reactive dyes are those of the formula Ia

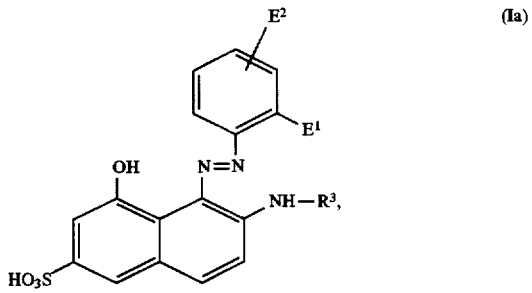

where

R$^3$, E$^1$ and E$^2$ each have the abovementioned meanings.

Reactive dyes of the formula Ia, where E$^1$ is a radical of the formula SO$_2$—Y, are of particular interest.

The novel reactive dyes of the formula I can be obtained by methods known per se.

For example, an aniline of the formula IIa or IIb

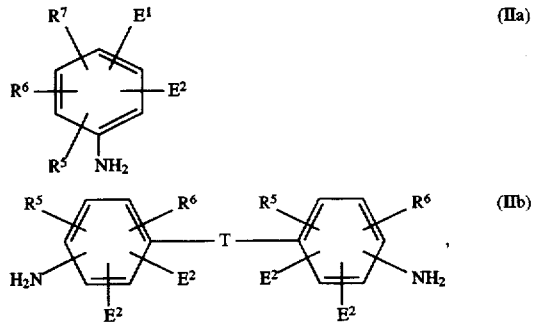

where R$^5$, R$^6{}_1$, R$^7$, E$^1$, E$^2$ and T each have the abovementioned meanings, can be diazotized or tetrazotized by a method known per se and coupled with an aminonaphthalene of the formula IIIa

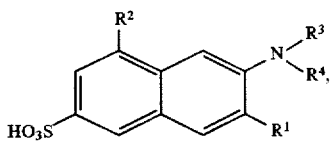

where R$^1$, R$^2$, R$^3$ and R$^4$ each have the abovementioned meanings.

The present application furthermore relates to aminonaphthalenes of the formula III

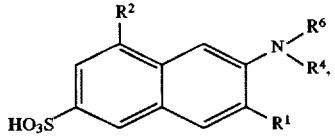

where

R$^1$ is hydrogen or hydroxysulfonyl,

R$^2$ is hydrogen or hydroxyl,

R$^6$ is carboxymethyl, hydroxysulfonylmethyl or a radical of the formula W$^1$—SO$_2$—Y or W$^2$(—SO$_2$—Y)$_2$, where W$^1$ is C$_1$-C$_4$-alkylene or unsubstituted or substituted phenylene, W$^2$ is a trivalent radical of a benzene ring which is unsubstituted or substituted and Y is vinyl or a radical of the formula C$_2$H$_4$—Q, where Q is a group which can be eliminated under alkaline reaction conditions, C$_5$-C$_7$-cycloalkyl or phenyl which is substituted by C$_1$-C$_4$-alkyl, C$_1$-C$_4$-alkoxy, carboxyl or a radical of the formula CONH—W$^1$—SO$_2$—Y or SO$_2$—Y, where W$^1$ and Y each have the abovementioned meanings, and R$^4$ is hydrogen or R$^4$ and R$^6$, together with the nitrogen atom linking them, form a 5-membered or 6-membered saturated heterocyclic radical which may have further hetero atoms.

Aminonaphthalenes of the formula III where R$^1$ is hydrogen are preferred.

Aminonaphthalenes of the formula III where R$^2$ is hydroxyl are also preferred.

Other preferred aminonaphthalenes are those of the formula III where R$^6$ is hydroxysulfonylmethyl.

The aminonaphthalenes of the formula III can be obtained by methods known per se. For example, a naphthalene derivative of the formula IV

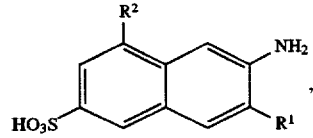

where R$^1$ and R$^2$ each have the abovementioned meanings, can be reacted with an amine of the formula V

where R$^4$ and R$^6$ each have the abovementioned meanings, in the presence of an alkali metal sulfite, for example sodium sulfite or potassium sulfite.

The novel reactive dyes of the formula I can be advantageously used for dyeing or printing hydroxyl-containing or nitrogen-containing organic substrates. Examples of such substrates are leather or fiber material which contains predominantly natural or synthetic polyamides or natural or regenerated cellulose. The novel dyes can preferably be used for dyeing and printing textile material based on wool or in particular on cotton. Dyeings in red hues are obtained.

Deep dyeings which have a very high fixation yield, very good lightfastness and excellent wet fastness properties, such as fastness to washing, to chlorine bleaches, to peroxide bleaches, to alkalis, to sea water or to perspiration, are obtained, particularly on substrates based on cellulose.

The examples which follow illustrate the invention.

EXAMPLE 1

0.1 mol of the compound of the formula

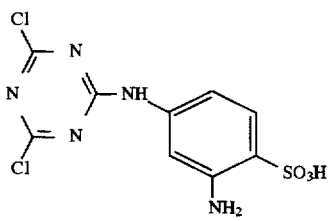

in the form of a 35% strength by weight aqueous solution was diazotized at from 0° to 5° C. with 25 ml of 30% strength by weight hydrochloric acid and 30 ml (0.1 mol) of 23% strength by weight aqueous sodium nitrite solution. 33.1 g (0.1 mol) of the compound of the formula

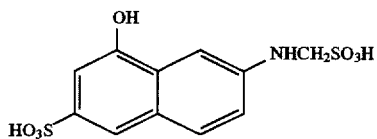

were then added, the pH being kept at from 2.5 to 3 by adding aqueous sodium acetate solution. After the end of the coupling, the pH was brought to 5–5.5 with sodium bicarbonate. The dye of the formula

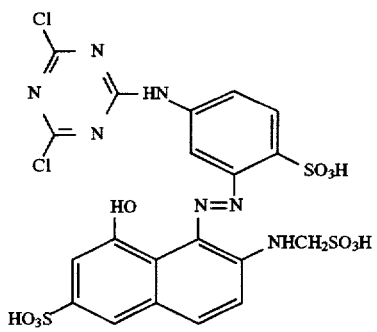

was isolated by salting out, filtering off and drying.
$\lambda_{max}$ (water): 523 nm

EXAMPLE 2

28.1 g (0.1 mol) of 1-amino-2-(2-sulfatoethylsulfonyl) benzene were stirred in 300 ml of ice water and diazotized by adding 10 ml of 30% strength by weight hydrochloric acid and 30 ml (0.1 mol) of 23% strength by weight aqueous sodium nitrite solution. A temperature of from 0° to 5 ° C. was maintained for 1.5 hours. 34.3 g (0.103 mol) of the compound of the formula

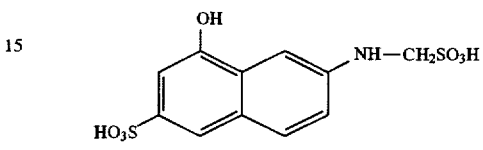

were then added, the pH being kept at 2.5 by adding aqueous sodium acetate solution. After the end of the coupling, the pH was brought to 5–5.5 with sodium bicarbonate. The dye of the formula

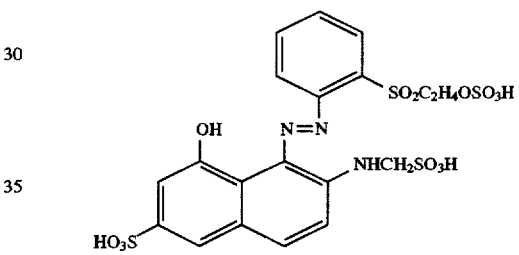

was isolated by salting out, filtering off and drying. It can also be isolated by spray-drying.

$\lambda_{max}$ (water): 530 nm

EXAMPLE 3

0.1 mol of the compound of the formula

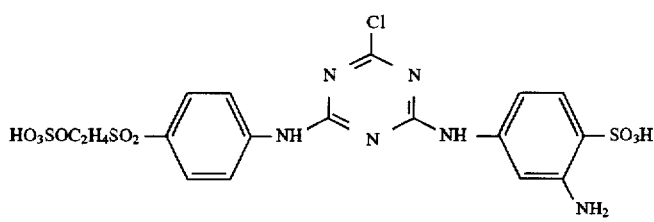

was stirred in 200 ml of ice water. Diazotization was effected at from 0° to 5° C. by adding 25 ml of 30% strength by weight hydrochloric acid and 30 ml (0.1 mol) of 23% strength by weight aqueous sodium nitrite solution. 33.3 g (0.1 mol) of the compound of the formula

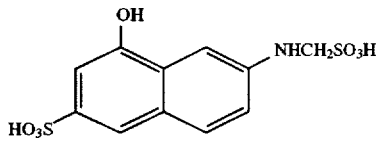

were then added, the pH being kept at 2.5–3 by adding aqueous sodium acetate solution. After the end of the coupling, the pH was brought to 5–5.5 with sodium bicarbonate. The dye of the formula

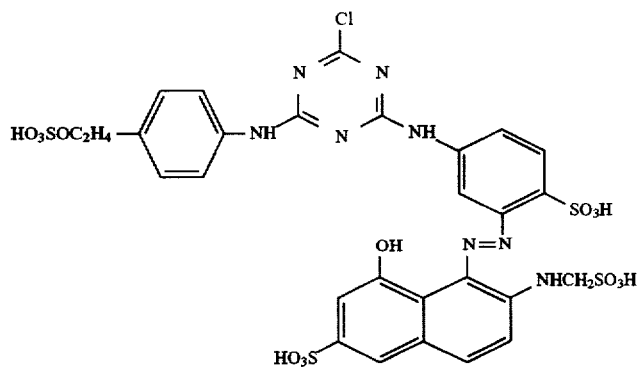

was isolated by salting out, filtering off and drying.
$\alpha_{max}$ (water): 520 nm

EXAMPLE 4

The dye of the formula

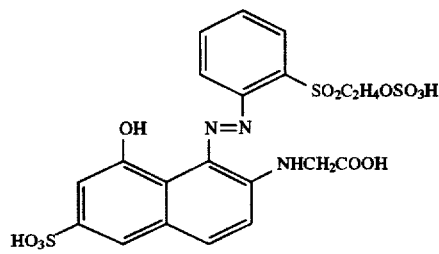

was obtained similarly to Example 2.
$\lambda_{max}$ (water): 530 nm

EXAMPLE 5

27.0 g (0.042 mol) of 3,3'-diamino-4,4'-bis(2-sulfatoethyl-sulfonyl)benzophenone were stirred in 200 ml of ice water, 30 ml of 10 N hydrochloric acid and 100 ml of glacial acetic acid were added and tetrazotization was effected at from 0° to 5° C. with 30 ml of a 23 % strength by weight aqueous sodium nitrite solution while stirring. After stirring had been carried out for 3 hours at from 0° to 5° C., the small excess of free nitrous acid was decomposed by adding amidosulfonic acid. Thereafter, 17.4 ml (0.087 mol) of an aqueous solution of the compound of the formula

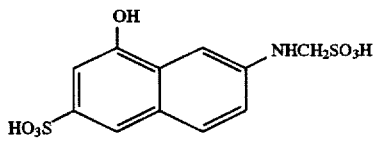

were added and the pH was kept at from 3 to 3.5 with sodium acetate. After the end of the reaction, the mixture was allowed to warm up to room temperature and the pH was brought to 5–5.5 with sodium carbonate. Potassium chloride was added to the reaction solution and stirring was carried out for 4 hours. The red precipitate was filtered off and dried. The dye of the formula

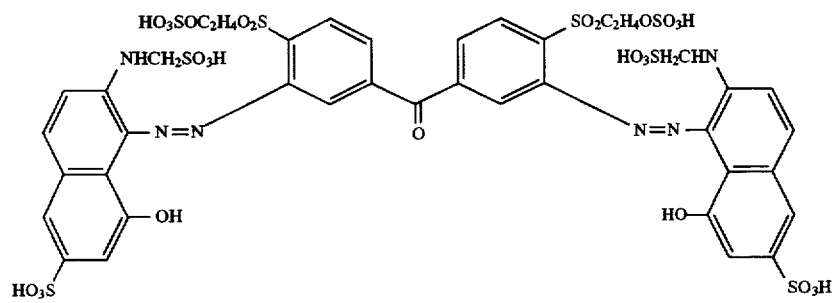

was obtained.
$\lambda_{max}$ (water): 534 nm
The dyes shown below are obtained in a similar manner.
EXAMPLE 6
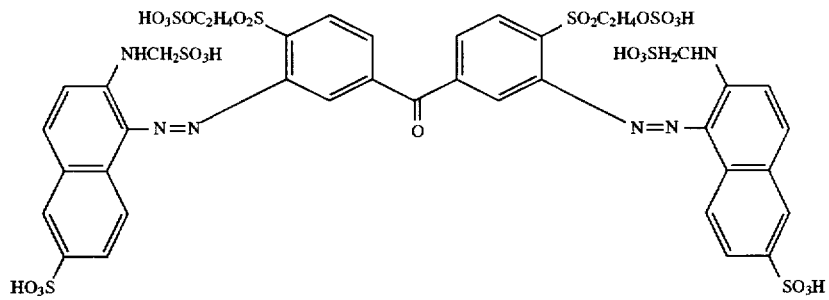
$\lambda_{max}$ (water): 508 nm
EXAMPLE 7
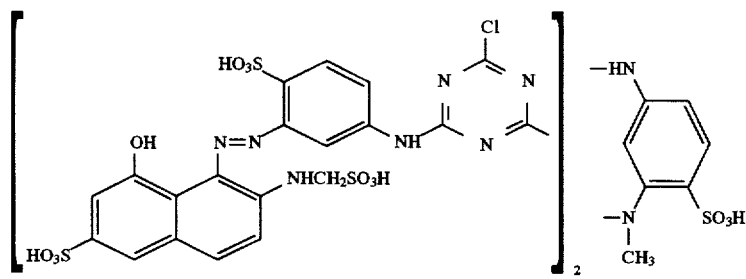
$\lambda_{max}$ (water): 522 nm
EXAMPLE 8
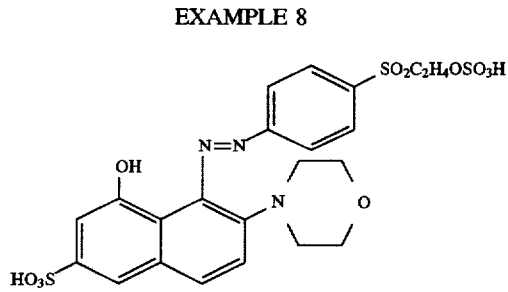
$\lambda_{max}$ (water): 514 nm
EXAMPLE 9
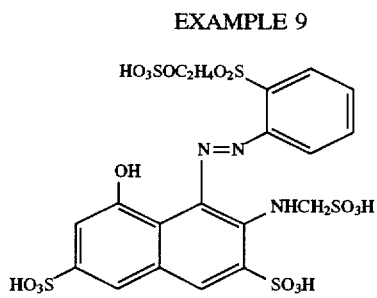
$\lambda_{max}$ (water): 526 nm
EXAMPLE 10
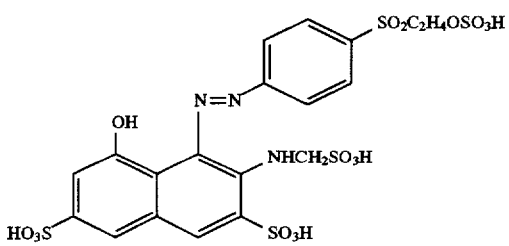
$\lambda_{max}$ (water): 518 nm
EXAMPLE 11
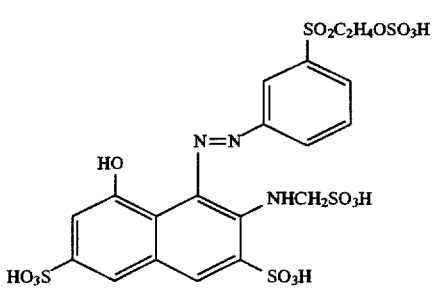
$\lambda_{max}$ (water): 528 nm

EXAMPLES 12 and 13

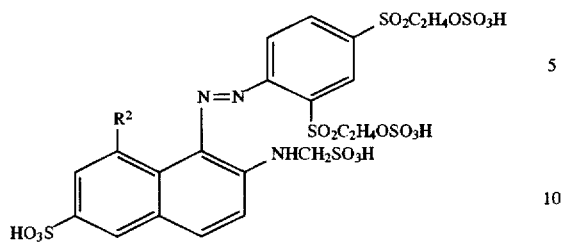

$R^2$ = OH  $\lambda_{max}$ (water): 564 nm (Example 12)

$R^2$ = H  $\lambda_{max}$ (water): 532 nm (Example 13)

| Ex. No. | $R^2$ | $R^3$ | Ring position of $SO_2C_2H_4OSO_3H$ | $R^5$ and ring position | $R^6$ and ring position | $\lambda_{max}$ (in water) [nm] |
|---|---|---|---|---|---|---|
| 14 | H | $CH_2SO_3H$ | 2 | H | H | 496 |
| 15 | H | $CH_2SO_3H$ | 3 | $SO_3H$ (6) | H | 522 |
| 16 | OH | —⟨C₆H₄⟩—COOH (ortho) | 2 | H | H | 534 |
| 17 | OH | —⟨C₆H₄⟩—$SO_2C_2H_4OSO_3H$ | 4 | H | H | 468 |
| 18 | OH | —⟨C₆H₄⟩—$SO_2C_2H_4OSO_3H$ | 2 | H | H | 535 |
| 19 | H | —⟨C₆H₄⟩—$SO_2C_2H_4OSO_3H$ | 4 | H | H | 506 |
| 20 | H | —⟨C₆H₄⟩—$SO_2C_2H_4OSO_3H$ | 2 | H | H | 508 |
| 21 | OH | $CH_2SO_3H$ | 3 | $SO_3H$ (4) | $SO_3H$ (6) | 494 |
| 22 | OH | $C_2H_4SO_2C_2H_4OSO_3H$ | 4 | H | H | 514 |
| 23 | OH | $C_2H_4SO_2C_2H_4OSO_3H$ | 3 | H | H | 506 |
| 24 | H | $CH_2SO_3H$ | 2 | $SO_3H$ (4) | H | 514 |
| 25 | OH | $CH_2SO_3H$ | 2 | $SO_3H$ (4) | H | 548 |
| 26 | H | $C_2H_4SO_2C_2H_4OSO_3H$ | 4 | H | H | 488 |

-continued

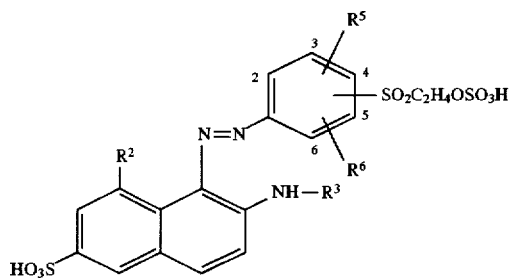

| Ex. No. | R² | R³ | Ring position of SO₂C₂H₄OSO₃H | R⁵ and ring position | R⁶ and ring position | λmax (in water) [nm] |
|---|---|---|---|---|---|---|
| 27 | H | —⟨C₆H₄⟩—SO₂C₂H₄OSO₃H | 3 | H | H | 494 |
| 28 | H | C₂H₄SO₂C₂H₄OSO₃H | 2 | H | H | 493 |
| 29 | OH | —⟨C₆H₁₁⟩ | 2 | H | H | 520 |
| 30 | H | CH₂SO₃H | 3 | SO₃H (4) | SO₃H (6) | 514 |
| 31 | H | CH₂SO₃H | 4 | SO₃H (2) | SO₃H (6) | 476 |
| 32 | OH | CH₂SO₃H | 4 | SO₃H (2) | SO₃H (6) | 490 |

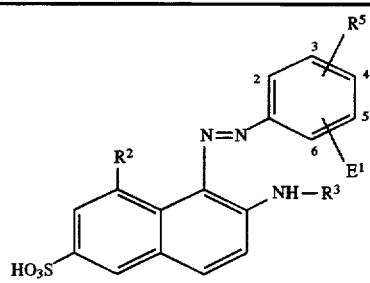

| Ex. No. | R² | R³ | E¹ and ring position | R⁵ and ring position | λmax (in water) [nm] |
|---|---|---|---|---|---|
| 33 | OH | CH₂SO₃H | [chlorotriazine-NH-C₆H₄-SO₂C₂H₄OSO₃H] | (3) H | 518 |
| 34 | OH | CH₂SO₃H | NHCONHC₃H₆SO₂C₂H₄OSO₃H | (3) SO₃H (6) | 520 |

-continued

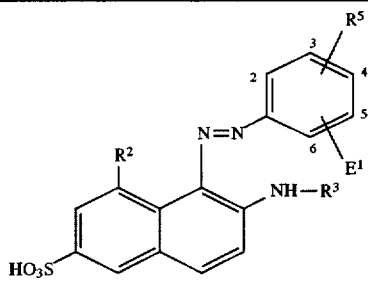

| Ex. No. | R² | R³ | E¹ and ring position | R⁵ and ring position | λmax (in water) [nm] |
|---|---|---|---|---|---|
| 35 | OH | CH₂SO₃H | (structure with Cl-triazine, NHC₂H₄SO₂C₂H₄OSO₃H, SO₂C₂H₄OSO₃H) | (3) SO₃H (2) | 522 |
| 36 | H | CH₂SO₃H | (structure with Cl-triazine, SO₂C₂H₄OSO₃H) | (3) SO₃H (6) | 484 |
| 37 | OH | CH₂SO₃H | CONHC₃H₆SO₂C₂H₄OSO₃H | (4) H | 520 |

We claim:

1. A reactive dye of the formula I

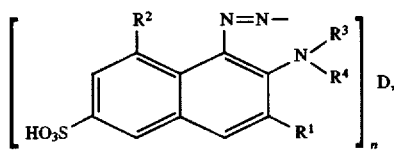

where n is 1 or 2,

R¹ is hydrogen or hydroxysulfonyl,

R² is hydrogen or hydroxyl,

R³ is carboxymethyl, hydroxysulfonylmethyl, a radical of the formula W¹—SO₂—Y or W²(—SO₂—Y)₂, where W¹ is C₁-C₄-alky-lene or unsubstituted or substituted phenylene, W² is a trivalent radical of a benzene ring which is unsubstituted or substituted and Y is vinyl or a radical of the formula C₂H₄—Q, where Q is a group which can be eliminated under alkaline reaction conditions, phenyl which is substituted by carboxyl or a radical of the formula CONH-W¹—SO₂—Y or SO₂—Y, where W¹ and Y each have the abovementioned meanings, or, if n is 2, R³ may furthermore be carboxy-C₂-C₄-alkyl or hydroxysulfonyl-C₂-C₄-alkyl, R⁴ is hydrogen or R³ and R⁴, together with the nitrogen atom linking them, form a 5-membered or 6-membered saturated, heterocyclic radical which may have further hetero atoms, and D, if n is 1, is a radical of the formula

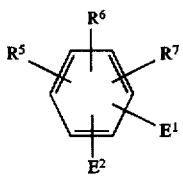

or, if n is 2, is a radical of the formula

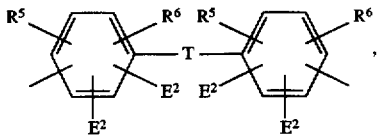

where R⁵, R⁶ and R⁷, independently of one another, are each hydrogen, C₁-C₄-alkyl, C₁-C₄-alkoxy or hydroxysulfonyl, E¹ is a heterocyclic mechanism or a mechanism from the aliphatic series, E² is hydrogen or E¹, and T is a bridge member, with the proviso that at least one mechanism is present in D.

2. A reactive dye as claimed in claim 1, wherein R¹ is hydrogen.

3. A reactive dye as claimed in claim 1, wherein R² is hydroxyl.

4. A reactive dye as claimed in claim 1, wherein R³ is hydroxysulfonylmethyl.

5. A reactive dye as claimed in claim 1, wherein R⁵, R⁶ and R⁷ are each hydrogen.

6. A reactive dye as claimed in claim 1, wherein $E^1$ is a halogen-substituted radical of 1,3,5-triazine or a radical of the formula $SO_2$—Y, where Y has the meanings stated in claim 1.

7. A reactive dye as claimed in claim 1, wherein T is a radical of the formula CO or $SO_2$ if n is 2.

8. A reactive dye as claimed in claim 1, wherein n is 1.

9. A reactive dye as claimed in claim 1, wherein $E^1$ is a radical of the formula $SO_2$—Y, where Y has the meanings stated in claim 1, and is ortho to the azo group.

10. A method of dyeing or printing hydroxyl-containing or nitrogen-containing organic substrates comprising applying a reactive dye as claimed in claim 1 to said substrate.

* * * * *